United States Patent [19]

Spencer et al.

[11] 4,355,049

[45] Oct. 19, 1982

[54] FLAVORING WITH 2-(α-MERCAPTOALKYL)-3-THIAZOLINE

[75] Inventors: Marcia D. Spencer, Valley Cottage; Thomas H. Parliment, New City, both of N.Y.; Denise A. Giordano, Danbury, Conn.

[73] Assignee: General Foods Corporation, White Plains, N.Y.

[21] Appl. No.: 290,624

[22] Filed: Aug. 6, 1981

[51] Int. Cl.$^3$ ............................................... A23L 1/231
[52] U.S. Cl. ..................................... 426/535; 548/146
[58] Field of Search ......................... 548/146; 426/535

[56] References Cited

U.S. PATENT DOCUMENTS

| | | | |
|---|---|---|---|
| 4,067,344 | 1/1978 | Vinals et al. | 131/17 |
| 4,243,688 | 1/1981 | Vock et al. | 426/535 |
| 4,256,776 | 3/1981 | Withycombe et al. | 426/535 |
| 4,263,332 | 4/1981 | Withycombe et al. | 426/535 |

*Primary Examiner*—Joseph M. Golian
*Attorney, Agent, or Firm*—Joseph T. Harcarik; Daniel J. Donovan

[57] ABSTRACT

A flavoring composition of 2-(α-mercaptoalkyl)-3-thiazoline when added to foodstuffs imparts or augments a meaty, sauteed onion flavor and aroma.

8 Claims, No Drawings

FLAVORING WITH 2-(α-MERCAPTOALKYL)-3-THIAZOLINE

BACKGROUND OF THE INVENTION

This invention relates to a composition which imparts or enhances the flavor of foodstuffs. More particularly a flavoring composition is discovered which imparts or enhances the meaty, sauteed onion flavor, character and aroma of foodstuffs. A process is also disclosed for preparing this flavoring composition.

SUMMARY OF THE INVENTION

Briefly, this invention involves adding as a flavoring composition an effective amount of either 2,4-dimethyl-2-(mercaptomethyl)-3-thiazoline or 2,4,5-trimethyl-2-(α-mercaptoethyl)-3-thiazoline to foodstuffs to impart or enhance a meaty, sauteed onion flavor and aroma in the foodstuffs. The flavoring composition is prepared by reacting 3-mercapto-2-butanone or mercaptoacetone in the presence of ammonia, ethanol and water.

DETAILED DESCRIPTION OF THE INVENTION

This invention is directed to a flavoring composition which provides unique flavor characteristics to foods. The flavoring composition is 2-(α-mercaptoalkyl)-3-thiazoline and has the following structure:

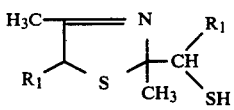

wherein $R_1$ is either hydrogen or a methyl group.

The flavor which this composition imparts is described as a meaty, sauteed onion flavor. This flavor is similar to that obtained upon braising a piece of beef with onions, i.e. a browned meaty flavor with a savory, oniony background (browned onion character). The flavoring composition is specific to the two above identified compounds to impart the desired flavor and aroma. Higher alkyl substitutions have resulted in substantially different flavors and aromas.

This flavoring composition can be effectively used in any one of a number of foodstuffs such as sauces, gravies, seasonings, soups, meat analogs or beverages. The level at which the flavoring compound is effective in foodstuffs is generally within the range of 0.05 to 50 parts per million, preferably 0.1 to 10 parts per million of the foodstuff.

A unique method of preparing the flavoring composition is also described. Basically it involves reacting either 3-mercapto-2-butanone or mercaptoacetone in the presence of ammonia (NH$_3$), ethanol and water. More specifically 2,4,5-trimethyl-2-(α-mercaptoethyl)-3-thiazoline has been prepared as follows: to 1 ml. of water and 3 ml. of 29% aqueous NH$_3$ adding dropwise a solution of 1.04 gms of 3-mercapto-2-butanone and 1.04 gms of ethanol (95%); stirring the mixture for one hour at room temperature; then extracting the flavoring compound with ether; concentrating on a rotary evaporator and purifying by gas chromatography or distillation.

The flavoring composition 2,4-dimethyl-2-(mercaptomethyl)-3-thiazoline has been prepared as follows: to 1 ml. of water and 3 ml. of 29% aqueous NH$_3$ buffered to a pH of 7 adding dropwise a solution of 1 gm of mercaptoacetone and 1 gm of ethanol (95%); stirring the mixture for one hour at room temperature; then extracting the flavoring compound with ether; concentrating on a rotary evaporator and purifying by gas chromatography or distillation.

When 2,4,5-trimethyl-2-(α-mercaptoethyl)-3-thiazoline was added at levels of 0.1 ppm and 1 ppm to a beef gravy or a chicken gravy a more meaty, sauteed onion flavor and aroma was imparted to the gravies. When 2,4-dimethyl-2-(mercaptomethyl)-3-thiazoline was added at levels of 0.1 ppm and 1 ppm to a beef gravy a savory, browned meat flavor and aroma was imparted to the gravy.

What is claimed:

1. A process for imparting or enhancing a flavor in a foodstuff comprising adding an amount of a flavoring composition chosen from the group consisting of 2,4-dimethyl-2-(mercaptomethyl)-3-thiazoline and 2,4,5-trimethyl-2-(α-mercaptoethyl)-3-thiazoline, to the foodstuff effective to augment or impart a meaty, sauteed onion flavor.

2. Process of claim 1 wherein the effective amount is within the range of 0.05 to 50 parts per million of the foodstuff.

3. Process of claim 2 wherein the effective amount is within the range of 0.1 to 10 parts per million of the foodstuff.

4. Process of claim 1 wherein the foodstuff is chosen from the group consisting of soup, sauce, seasoning, gravy, meat analog or beverage.

5. A foodstuff comprising an amount of a flavoring composition chosen from the group consisting of 2,4-dimethyl-2-(mercaptomethyl)-3-thiazoline and 2,4,5-trimethyl-2-(α-mercaptoethyl)-3-thiazoline effective to impart or enhance a meaty, sauteed onion flavor in the foodstuff.

6. Foodstuff of claim 5 wherein the effective amount is within the range of 0.05 to 50 parts per million of the foodstuff.

7. Foodstuff of claim 6 wherein the effective amount is within the range of 0.1 to 10 parts per million of the foodstuff.

8. Foodstuff of claim 7 wherein the foodstuff is chosen from the group consisting of soup, sauce, gravy, meat analog or beverage.